(12) United States Patent
Jang et al.

(10) Patent No.: US 8,571,827 B2
(45) Date of Patent: Oct. 29, 2013

(54) SMART FOOTWEAR AND OPERATING METHOD THEREOF

(75) Inventors: Jae Won Jang, Daejeon (KR); Sa Kwang Song, Daejeon (KR); Ho Youl Jung, Daejeon (KR); Min Ho Kim, Daejeon (KR); Soo Jun Park, Seoul (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 326 days.

(21) Appl. No.: 12/963,575

(22) Filed: Dec. 8, 2010

(65) Prior Publication Data

US 2011/0153261 A1 Jun. 23, 2011

(30) Foreign Application Priority Data

Dec. 21, 2009 (KR) ........................ 10-2009-0128368

(51) Int. Cl.
*G01P 15/00* (2006.01)
*G08B 21/00* (2006.01)
*A61B 5/103* (2006.01)
*G01S 1/00* (2006.01)

(52) U.S. Cl.
USPC ............ 702/141; 340/669; 600/592; 701/408

(58) Field of Classification Search
USPC ......... 702/141, 33, 41–43, 57, 64–65, 81, 84, 702/127, 138–140, 150–153, 173, 182–183, 702/188–189; 73/1.37–1.38, 1.75, 1.77, 73/1.79, 488, 492–493, 503.3, 73/504.02–504.03, 514.01–514.02, 760, 73/763, 768, 775, 781; 33/1 N, 1 PT, 3 R; 340/3.1, 573.1, 665–666, 669; 342/357.25, 450; 600/592; 701/408, 701/468

See application file for complete search history.

(56) References Cited

U.S. PATENT DOCUMENTS

| 2008/0276493 A1 | 11/2008 | Dunias |
| 2009/0238400 A1 | 9/2009 | Im |

FOREIGN PATENT DOCUMENTS

| JP | 2005-237926 A | 9/2005 |
| KR | 10-0647818 B1 | 11/2006 |
| KR | 10-2007-0037449 A | 4/2007 |
| KR | 10-2009-0049572 A | 5/2009 |
| KR | 10-2009-0072178 A | 7/2009 |
| KR | 10-2009-0080672 A | 7/2009 |
| WO | WO 2007/081905 A1 | 7/2007 |

OTHER PUBLICATIONS

Benocci et al., A Wireless System for Gait and Posture Analysis Based on Pressure Insoles and Inertial Measurement Units, Apr. 1-3, 2009, 3rd International Conference on Pervasive Health, 6 pp.*
Abstract of Benocci et al. reference, Jan. 12, 2013, 2 pp.*

* cited by examiner

*Primary Examiner* — Toan Lee

(57) ABSTRACT

Smart footwear includes: a film type insole sensor measuring a change of force applied by a user's foot, as a resistance value; an acceleration sensor measuring an acceleration value according to a change in the motion of the user's foot; and a microcontroller estimating the user's current condition and the quantity of motion based on the resistance value and the acceleration value, and generating user condition information and quantity of motion information.

16 Claims, 3 Drawing Sheets

SMART FOOTWEAR AND OPERATING METHOD THEREOF

CROSS-REFERENCE TO RELATED APPLICATIONS

This application claims the priority of Korean Patent Application No. 10-2009-0128368 filed on Dec. 21, 2009, in the Korean Intellectual Property Office, the disclosure of which is incorporated herein by reference.

BACKGROUND OF THE INVENTION

1. Field of the Invention

The present invention relates to smart footwear and operating method thereof and, more particularly, to smart footwear capable of measuring the activity and quantity of motion of elderly residents of retirement villages or nursing homes, and an operating method thereof.

2. Description of the Related Art

As modern society is transitioning toward an aging society, the numbers of aged people who reside in nursery homes or retirement villages is increasing. Due to the development of health care and IT technology, those who live in such facilities can have periodical checkups of their physical condition and may receive additional help as necessary. Through these techniques, bio-information including pulse, blood pressure, blood-sugar levels, and the like, may be monitored, or the basic daily lives of the elderly can be monitored through a positioning (or location tracking) technique such as RFID (Radio-Frequency Identification), a USN (Ubiquitous Sensor Network), and the like, whereby a healthy lifestyle can be induced and help can be offered when an abnormal symptom or an emergency occurs.

These techniques are simply focused on checking the physical condition of the elderly in indoor places or are focused on how to quickly cope with an accident or a dangerous situation that takes place.

However, in order for the elderly to live a better life in their old age, they need to actively participate in social activities as well as being in good physical condition, without a sense of isolation. If the elderly live solely in a single room or do not positively participate in workouts or group activities, those lives cannot be considered to be good healthy lives.

The related art allows for the measurement of the quantity of motion or caloric consumption by using a passometer including an acceleration sensor, a piezoelectric sensor, or the like, or an activity measurement device, or broadly analogizing a lifestyle, or the behaviors of everyday lives by using a positioning technique such as a USN, RFID, Wi-Fi, GPS, and the like.

However, these techniques bring about user inconvenience in that users must continually wear new devices and users may have possible reluctance in that they might feel as if they are being monitored constantly, and if location information and the quantity of motion are not combined, there is a limitation in detecting users' activities and a sense of isolation.

SUMMARY OF THE INVENTION

An aspect of the present invention provides smart footwear capable of measuring elderly people's level of activity and sense of isolation in living daily lives, without causing inconvenience or reluctance with respect to the wearing of a new device, and an operating method thereof.

According to an aspect of the present invention, there is provided smart footwear including: a film type insole sensor measuring a change of force applied by a user's foot, as a resistance value; an acceleration sensor measuring an acceleration value according to a change in the motion of the user's foot; and a microcontroller estimating the user's current condition and the quantity of motion based on the resistance value and the acceleration value, and generating user condition information and quantity of motion information.

According to another aspect of the present invention, there is provided a method for operating smart footwear that is able to measure the user's activity and quantity of motion, including: measuring a change of force applied by the user's foot, as a resistance value by using a film type insole sensor; measuring an acceleration value according to a change in the motion of the smart footwear by using an acceleration sensor; and estimating the user's current condition and quantity of motion based on the resistance value and the acceleration value, and generating user condition information and quantity of motion information.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
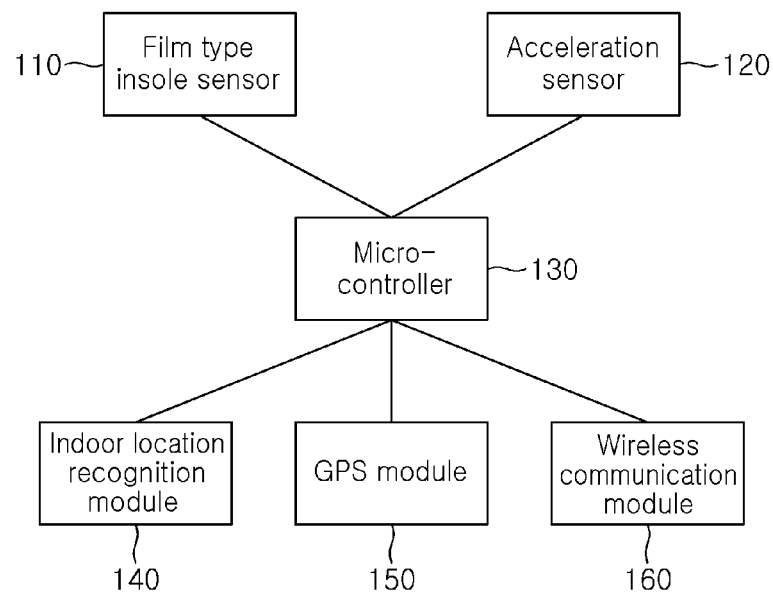
FIG. 1 is a schematic block diagram of a module installed at an inner side of smart footwear according to an exemplary embodiment of the present invention.

Exemplary embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions may be exaggerated for clarity, and the same reference numerals will be used throughout to designate the same or like components.

FIG. 1 is a schematic block diagram of a module installed at an inner side of smart footwear according to an exemplary embodiment of the present invention.

With reference to FIG. 1, smart footwear according to an exemplary embodiment of the present invention includes a film type insole sensor 110, an acceleration sensor 120, a microcontroller 130, and the like. Here, the film type insole sensor 110 and the acceleration sensor 120 are installed at an inner side of footwear. Namely, when the user wears footwear, the contact areas of the two sensors are positioned under the user's sole. The two sensors are connected to an analog-to-digital converter (ADC) terminal of the microcontroller 130, and the acceleration sensor 12 is configured as a PCB along with the microcontroller 130.

When the user is on the move, the film type insole sensor 110 measures a change in a force applied by the user's foot, as a resistance value, and outputs the measured resistance value to the ADC terminal of the microcontroller 130.

With reference to FIG. 1, smart footwear according to an exemplary embodiment of the present invention includes a film type insole sensor 110, an acceleration sensor 120, a microcontroller 130, and the like. Here, the 25 film type insole sensor 110 and the acceleration sensor 120 are installed at an inner side of footwear. Namely, when the user wears footwear, the contact areas of the two sensors are positioned under the user's sole. The two sensors are connected to an analog-to-digital converter 5 (ADC) terminal of the microcontroller 130, and the acceleration sensor 120 is configured as a PCB along with the microcontroller 130.

The microcontroller 130 digitalizes the resistance value and the acceleration value output from the film type insole sensor 110 and the acceleration sensor 120, respectively, through the internal ADC. The microcontroller 130 analyzes the digitalized resistance value and acceleration value to estimate the user's current condition and quantity of motion and generates user condition information and quantity of motion information. Namely, the microcontroller 130 analyzes the digitalized resistance value to classify the user's current condition as one of 'motion', 'no motion', 'walking', 'running', and the like, and generates user condition information based thereon. Also, the microcontroller 130 estimates a user's quantity of motion by using the digitalized acceleration value and the user's weight, and generates user quantity of motion information based thereon. In an exemplary embodiment of the present invention, the method of analyzing the resistance value to recognize user's current condition will later be described with reference to FIG. 2.

In addition, the smart footwear according to an exemplary embodiment of the present invention may further include an indoor location recognition module 140 and a GPS module 150 that detect the location of a user wearing the smart footwear.

The indoor location recognition module 140 may detect the user's location in a room through short-range communication such as a USN (Ubiquitous Sensor Network), RFID (Radio-Frequency Identification), Wi-Fi, ZigBee™, Bluetooth™, and the like, and generates user location information. In detail, the indoor location recognition module 140 performs communication with nodes installed in a building such as a room in a house, a restaurant, a resting place (e.g., lounge), a building foyer, a gym or health club, and the like, to detect the user's location and generate user location information.

When the user is located outside, so that his location cannot be recognized by the indoor location recognition module 140, the GPS module 150 detects the user's location through GPS and generates user location information.

The smart footwear according to an exemplary embodiment of the present invention may further include a wireless communication module 160 or the like.

The wireless communication module 160 periodically transmits the user condition information and quantity of motion information generated by the microcontroller 130 and the user location information generated by the indoor location recognition module 140 or the GPS module 150 to an external server through short-range communication including a USN, RFID, Wi-Fi, ZigBee™, Bluetooth™, and the like. Here, the wireless communication module 160 may be integrally formed with the indoor location recognition module 140, or may transmit the user condition information, quantity of motion information and location information to the external server through a mobile communication network, besides the short-rage communication.

The external server may analyze the quantity of motion and activity matters according to the user's location by using the user condition information, quantity of motion information, and location information received from the wireless communication module 160.

Figure 2:
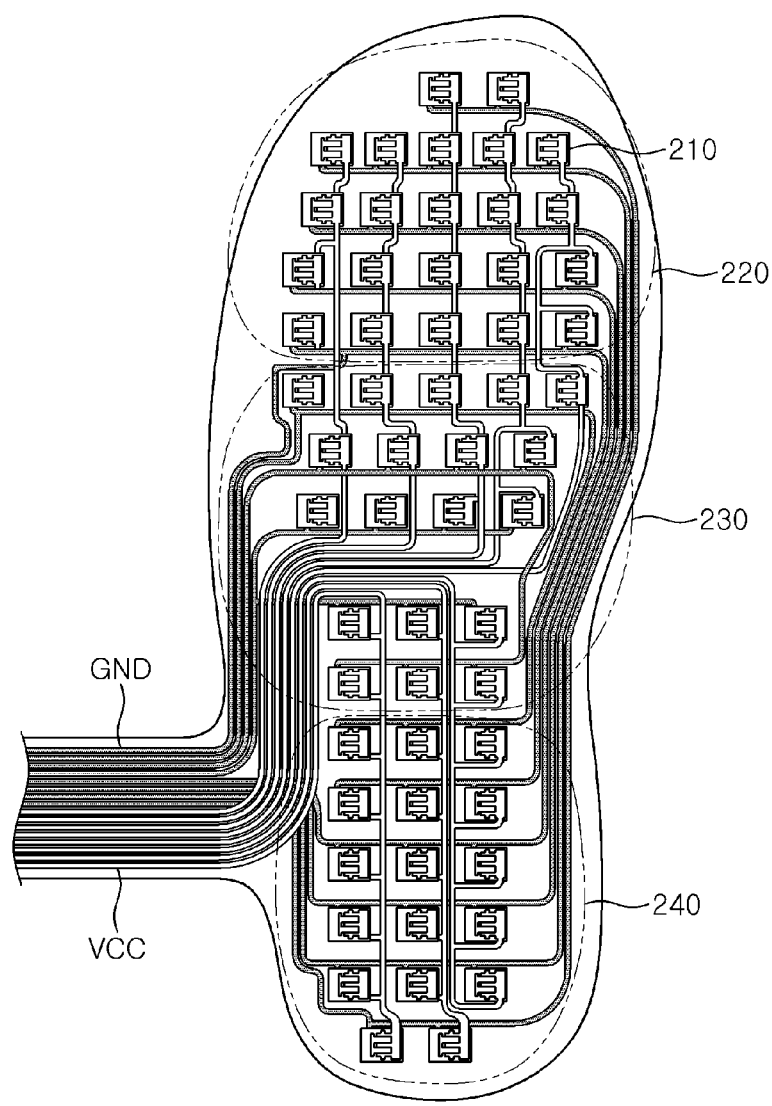
FIG. 2 illustrates the structure of a film type insole sensor installed on the bottom of the smart footwear according to an exemplary embodiment of the present invention.

FIG. 2 illustrates the structure of a film type insole sensor installed on the bottom of the smart footwear according to an exemplary embodiment of the present invention.

With reference to FIG. 2, the film type insole sensor 110 according to an exemplary embodiment of the present invention includes a plurality of cells (e.g., fifty-five cells) 210, and the voltage (VCC) and ground (GND) terminals of each cell 210 are connected to the microcontroller 130.

The film type insole sensor 110 including the plurality of cells 210 is divided into a plurality of areas including an upper portion 220 of the user's toe part, a middle portion 230 of the arched part of the user's sole, and a lower end portion 240 of the user's heel. Accordingly, in an exemplary embodiment of the present invention, the user's current condition is estimated by comparing the magnitude of forces applied to the respective areas. Namely, the magnitudes of forces applied to the plurality of areas vary according to when the user does not wear the footwear, when the user is standing, and when the user is seated. For example, when the user walks, the axis of force moves from the user's heel part to the user's toe part through the arch part, generally during a period of about 0.5 seconds.

Figure 3:
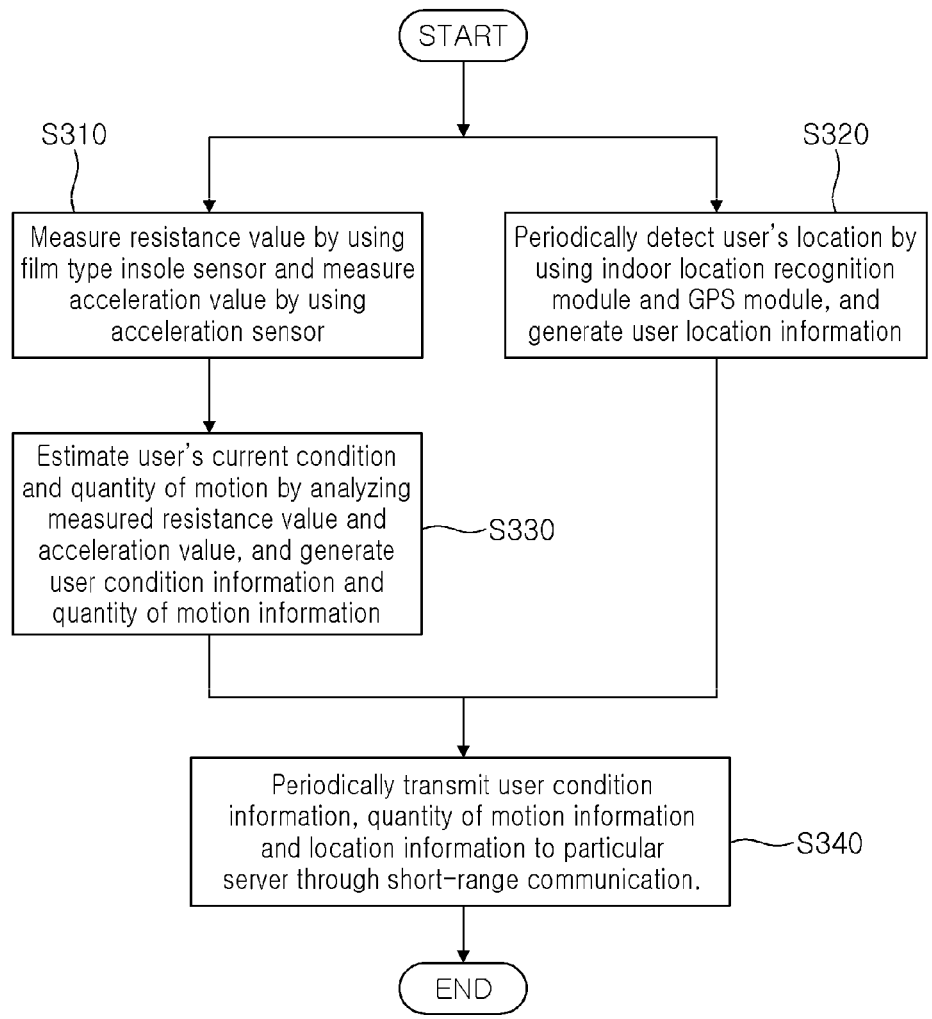
FIG. 3 is a flow chart illustrating the process of a method for operating smart footwear according to an exemplary embodiment of the present invention.

FIG. 3 is a flow chart illustrating the process of a method for operating smart footwear according to an exemplary embodiment of the present invention.

With reference to FIG. 3, a change in the force applied by the user's foot is measured as a resistance value by using the film type insole sensor 110, and an acceleration value according to a change in the motion of the smart footwear is measured by using the acceleration sensor 120 (S310). At the same time, the user's location is periodically detected by using the indoor location recognition module 140 and the GPS module 150, and user location information is generated (S320). Here, when the user is located in a building such as a room in a house, a restaurant, a resting place (e.g., lounge), a building foyer, a gym or health club, and the like, the user's location is detected by using the indoor location recognition module 140, and when the user is located outside, so his location cannot be recognized, the user's location is detected by using the GPS module 150.

Subsequently, the measured resistance value and acceleration value are analyzed so as to estimate the user's current condition and quantity of motion, and user condition information and quantity of motion information are generated (S330).

In detail, the user's current condition is classified into 'motion', 'no motion', 'walking', 'running', and the like, by analyzing the measured resistance value, based on which, the user condition information is generated. Namely, a user's current condition such as when the user does not wear the footwear, when the user is standing, and when the user is seated, or the like, is estimated by comparing the sizes of forces applied to the plurality of areas of the film type insole sensor 110 as shown in FIG. 2, and user condition information is generated.

In addition, in order to infer an accurate value of the quantity of motion, various variables including the user's weight, height, age, and the like, may be used. In an exemplary embodiment of the present invention, the quantity of motion is estimated by using the user's weight. Namely, the acceleration value is measured by using an equation $SVM = \sqrt{x_i^2 + y_i^2 + z_i^2}$ according to a change in the three-axes (X axis, Y axis, and Z axis 0) of the acceleration sensor 120, the user's quantity of motion is estimated by using the measured acceleration value and the user's weight, and user quantity of motion information is then generated.

Finally, the user's condition information, quantity of motion information, and individual pieces of location information such as 'ID/no motion/room of resident', 'ID/walking/8Kcal/resting place', and 'ID/running/15Kcal/health club', and the like, are periodically transmitted to the external server through short-range communication including the USN, RFID, Wi-Fi, ZigBee™, Bluetooth™, and the like. (S340).

The external server may analyze the quantity of motion and activity matters according to the user's location by using the received user condition information, quantity of motion information, and location information. For example, the external server may analyze the user's movement (e.g., room→restaurant→resting place→room→playground→restaurant→room) by using the received user condition information, quantity of motion information, and location information, and also analyze how actively the user is participating in group activities, how much exercise he or she is doing, how long he or she has been alone, and the like.

In addition, by analyzing data for a long period of time, the external server may infer the user's physical condition, lifestyle, a change in sociability, and the like.

As set forth above, according to exemplary embodiments of the invention, because footwear that is capable of recognizing the quantity of motion and location of the elderly residing in retirement villages or nursery homes is provided, the activity and sociability of the aged in the daily lives such as exercise facilities or recreation facilities.

In addition, the elderly can be induced to have a healthy lifestyle while minimizing their reluctance and discomfort toward new device.

While the present invention has been shown and described in connection with the exemplary embodiments, it will be apparent to those skilled in the art that modifications and variations can be made without departing from the spirit and scope of the invention as defined by the appended claims.

What is claimed is:

1. Smart footwear comprising:
   a film type insole sensor measuring a change of force applied by a user's foot as a resistance value;
   an acceleration sensor measuring an acceleration value according to a change in a motion of the user's foot;
   a microcontroller estimating a current condition of the user and a quantity of motion based on the resistance value and the acceleration value, and generating user condition information and quantity of motion information; and
   a location recognition module periodically detecting a location of the user and generating location information.

2. The smart footwear of claim 1, further comprising:
   a wireless communication module configured to periodically transmit the user's condition information, the quantity of motion information, and the location information to an external server through short-range communication.

3. The smart footwear of claim 2, wherein the external server analyzes the quantity of motion and activity matters according to the user's location by using the user's condition information, the quantity of motion information and the location information.

4. The smart footwear of claim 1, wherein the location recognition module comprises:

an indoor location recognition module configured to detect the user's location in a room through short-range communication and generate location information; and
   a GPS module configured to detect the user's location outside a building by using GPS and generate location information.

5. The smart footwear of claim 4, wherein the indoor location recognition module detects a user's location in a room using any of a Ubiquitous Sensor Network (USN) and Radio-Frequency Identification (RFID).

6. The smart footwear of claim 1, wherein contact areas of the film type insole sensor and the acceleration sensor are positioned under the user's sole.

7. The smart footwear of claim 1, wherein the acceleration sensor and the microcontroller are each configured as a PCB.

8. The smart footwear of claim 1, wherein the film type insole sensor comprises a plurality of cells, and voltage and ground terminals of each cell are coupled to the microcontroller.

9. The smart footwear of claim 8, wherein the film type insole sensor is divided into a plurality of areas comprising an upper portion corresponding to a toe part, a middle portion corresponding to an arch part of a sole, and a lower portion corresponding to a heel part.

10. The smart footwear of claim 9, wherein the microcontroller compares an amount of force applied to the plurality of areas to analyze an axial movement of the user, and estimates the user's current condition.

11. The smart footwear of claim 1, wherein the microcontroller estimates the user's quantity of motion based on the acceleration value and a weight of the user.

12. A method for operating smart footwear that is able to measure an activity of a user and a quantity of motion, the method comprising:
    measuring a change in force applied by a foot of the user as a resistance value by using a film type insole sensor;
    measuring an acceleration value according to a change in a motion of the smart footwear by using an acceleration sensor;
    estimating a current condition of the user and the quantity of motion based on the resistance value and the acceleration value, and generating user condition information and quantity of motion information; and
    periodically detecting a location of the user and generating location information.

13. The method of claim 12, wherein, in measuring the change in the force applied by the user's foot, as a resistance value, amounts of forces applied to a plurality of areas of the film type insole sensor are compared to analyze an axial movement of the user and estimate the user's current condition.

14. The method of claim 12, wherein, in measuring the acceleration value according to a change in the motion of the smart footwear, the user's quantity of motion is estimated by using the acceleration value and a weight of the user.

15. The method of claim 12, further comprising:
    analyzing the quantity of motion and activities according to the user's location based on the user's condition information, the quantity of motion information, and the location information.

16. The method of claim 15, wherein, in generating the location information, when the user is located in a room, the user's location is detected through short-range communication, and when the user is located outside, the user's location is detected by using a GPS.

* * * * *